United States Patent
Byun et al.

(10) Patent No.: US 10,253,347 B2
(45) Date of Patent: Apr. 9, 2019

(54) METHOD OF SCREENING FOR MICROORGANISM HAVING ENHANCED CELLULOSE PRODUCTIVITY

(71) Applicant: Samsung Electronics Co., Ltd., Suwon-si, Gyeonggi-do (KR)

(72) Inventors: Jongwon Byun, Suwon-si (KR); Soonchun Chung, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 200 days.

(21) Appl. No.: 15/228,162

(22) Filed: Aug. 4, 2016

(65) Prior Publication Data
US 2017/0145469 A1    May 25, 2017

(30) Foreign Application Priority Data
Nov. 19, 2015  (KR) .......................... 10-2015-0162845

(51) Int. Cl.
*C12P 19/04* (2006.01)
*C12Q 1/04* (2006.01)

(52) U.S. Cl.
CPC ................ *C12Q 1/04* (2013.01); *C12P 19/04* (2013.01)

(58) Field of Classification Search
None
See application file for complete search history.

(56) References Cited

U.S. PATENT DOCUMENTS

| | | | |
|---|---|---|---|
| 5,962,277 A | 10/1999 | Watanabe et al. | |
| 2015/0376666 A1 | 12/2015 | Tajima et al. | |

FOREIGN PATENT DOCUMENTS

| | | | |
|---|---|---|---|
| JP | 11-187896 A | 7/1999 | |
| JP | 2002-262898 A | 9/2002 | |
| JP | 5752332 B2 | 5/2015 | |
| WO | WO 2005/003366 A1 | 1/2005 | |
| WO | WO-2014104318 A1 * | 7/2014 | ............. C12P 19/04 |

OTHER PUBLICATIONS

Kouda "Effect of Agitator Configuration on Baceterial Cellulose Productivity", Journal of Fermentation and Bioengineering, vol. 83, No. 4 371-376, 1997. (Year: 1997).*
Dayal "Effect of media components on cell growth and bacterial cellulose production from Acetobacter aceti MTCC 2623", Carbohydrate Polymers, 94, 2013. (Year: 2013).*
Warren et al., "Continuum between Sorption and Precipitation of Fe(III) on Microbial Surfaces", *Environmental Science & Technology*, 32(15): 2331-2337 (1998).
Toyosaki et al., "Screening of Bacterial Cellulose-producing *Acetobacter* Strains for Agitated Culture," *Biosci Biotech. Biochem.*, vol. 59 (8) pp. 1498-1502 (1995).

* cited by examiner

*Primary Examiner* — Louise W Humphrey
*Assistant Examiner* — Charles Zoltan Constantine
(74) *Attorney, Agent, or Firm* — Leydig, Voit & Mayer, Ltd.

(57) ABSTRACT

Provided is a method of screening for a microorganism having enhanced cellulose productivity.

12 Claims, 2 Drawing Sheets

METHOD OF SCREENING FOR MICROORGANISM HAVING ENHANCED CELLULOSE PRODUCTIVITY

CROSS-REFERENCE TO RELATED APPLICATION

This application claims the benefit of Korean Patent Application No. 10-2015-0162845, filed on Nov. 19, 2015, in the Korean Intellectual Property Office, the entire disclosure of which is hereby incorporated by reference.

BACKGROUND

1. Field

The present disclosure relates to a method of screening for a microorganism having enhanced cellulose productivity.

2. Description of the Related Art

Cellulose has a ribbon-like bundle structure stabilized by hydrogen bonds between long chains of beta-D-glucopyranose (β-D-glucopyranose) units joined through beta-1,4-glucoside (β-1,4-glucoside) bonds.

Microbial cellulose consists of only cellulose, unlike plant cellulose containing hemicellulose, pectin, lignin, etc. Therefore, pure cellulose free from impurities can be obtained from microorganisms. Since microbial cellulose has excellent biocompatibility and mechanical properties, it may be applied to a wide variety of fields, such as the medical field, beauty products, food, electrical and electronics, among many others. However, its application has been restricted because of the absence of microorganisms having satisfactory cellulose productivity.

With advances in metabolic engineering, there have been many attempts to prepare microorganisms having high cellulose productivity. Up to now, there have been no genetic manipulation tools available for microorganisms producing cellulose, and thus, random mutagenesis has been commonly used to develop such microorganisms. Accordingly, there is a demand for a method of more efficiently screening for a microorganism strain having enhanced cellulose productivity from numerous candidate mutant strains prepared by random mutagenesis.

SUMMARY

One aspect of the invention provides a method of screening for a microorganism having enhanced cellulose productivity.

Another aspect of the invention provides a method of producing cellulose using the screened microorganism.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
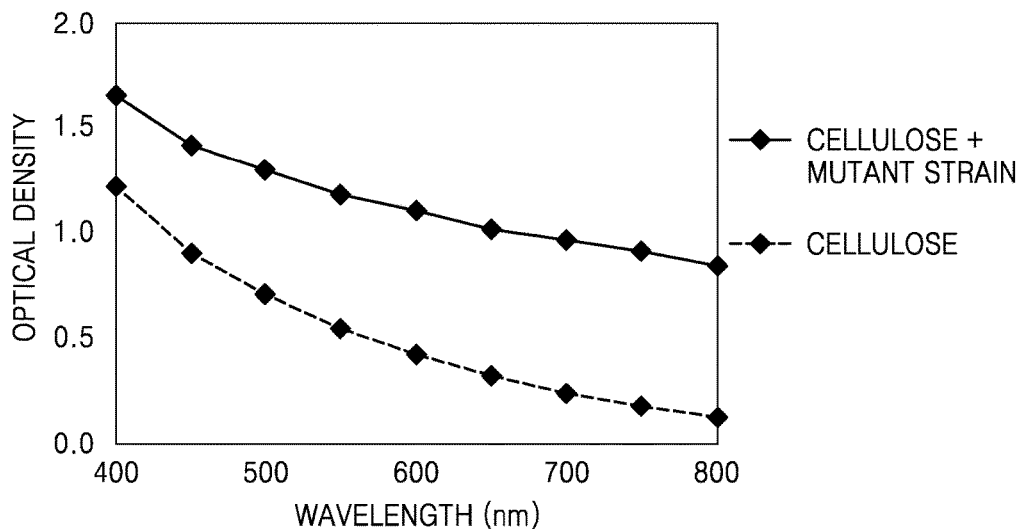
FIG. 1 shows results of measuring an optical density of a cellulose-producing strain in a visible light range.

One aspect of the invention provides a method of screening for a microorganism having enhanced cellulose productivity, the method including: culturing microorganisms having cellulose productivity to obtain cultures containing the respective microorganisms and cellulose; measuring, simultaneously or sequentially, optical density A and optical density B of the cultures and obtaining a ratio of optical density A/optical density B with respect to cultures that have an optical density A greater than that of a control group; and selecting a microorganism that has a ratio of optical density A/optical density B being greater than that of the control group as a microorganism having enhanced cellulose productivity. The optical density A is measured at a first wavelength in a visible light range, and the optical density B is measured at a second wavelength greater than the first wavelength in the visible light range. The first wavelength may be referred to as a short wavelength and the second wavelength may be referred to as a long wavelength. The microorganisms that are cultured may include one or more test or mutant microorganisms and one or more control microorganisms. Each microorganism is cultured to provide a plurality of cultures from which the microorganism(s) with the greatest cellulose production can be selected on the basis of a ratio of optical densities.

The microorganism may be *Aerobacter* sp., *Acetobacter* sp., *Achromobacter* sp., *Agrobacterium* sp., *Alacaligenes* sp., *Azotobacter* sp., *Pseudomonas* sp., *Rhizobium* sp., *Sarcina* sp., or *Gluconacetobacter* sp. The microorganism may be, for example, a microorganism belonging to *Gluconacetobacter* sp. The microorganism may be *Gluconacetobacter xylinus*. *Gluconacetobacter xylinus* may be also named *Acetobacter xylinum* or *Komagataeibacter xylinus*.

The microorganism having cellulose productivity may include a mutated microorganism or a recombinant microorganism. The term "mutated" or "modified" means that modification occurs at a genetic level, compared to a non-modified control group. The mutation may be a random or site-specific mutation. The mutation may include mutations caused by addition, deletion, and/or substitution of nucleotides constituting a gene. The mutated microorganism may include a naturally occurring mutated microorganism and/or an artificially mutated microorganism. The mutated microorganism may be prepared by inducing mutations in a naturally occurring microorganism. The mutated microorganism may be produced by random mutagenesis or directed mutagenesis. The mutated microorganism may be produced by nucleic acid shuffling or synthetic shuffling. The random mutagenesis may be caused by chemical treatment, UV treatment, error-prone PCR, or DNA shuffling.

In the method of screening for a microorganism having enhanced cellulose productivity, the control group may be a non-genetically modified microorganism of the same type or a non-mutated microorganism of the same type. The control group may be also called a parent strain. The control group may be a microorganism having cellulose productivity without genetic modification or mutagenesis. Further, the microorganism having enhanced cellulose productivity may be a microorganism having enhanced cellulose productivity, compared to that of the control group.

In the culturing, appropriate culture conditions may be determined by those skilled in the art. The culturing may be performed in static culture or agitated culture. A medium used in the culturing may be any general medium suitable for growth of the microorganism, such as a minimal or complex medium containing appropriate supplements. The suitable medium may be purchased from a commercially available source or prepared by a known preparation method. The medium may include ingredients selected from the group consisting of a carbon source, a nitrogen source, salts, trace elements, and combinations thereof. The carbon source may include monosaccharides, disaccharides and/or polysaccharides. The nitrogen source may be amino acids, amides, amines, nitrate, or ammonium salts. The medium may be a Hestrin-Schramm (HS) medium, a modified HS medium, an LB medium, modified LB medium, an YPD medium, a modified YPD medium, or a defined medium.

The culturing may be performed under aerobic conditions. The culturing temperature may be about 20° C. to about 40° C., about 22 to about 38° C., or about 25 to about 37° C. pH of the culture medium may be about 4.0 to about 7.5, about 4.0 to about 7.0, or about 4.5 to about 7.0.

The culturing may be performed on a microplate. In respective wells of the microplate, different types of mutated microorganisms may be cultured. The microplate may be a 96-well microplate. The culturing may be performed on 2 or more, 3 or more, 4 or more, 5 or more, 6 or more, 7 or more, 8 or more, 9 or more, or 10 or more of the microplates at the same time. The culturing may be performed by a high throughput screening (HTS) system. The amount of the medium per well may be about 0.1 to about 0.25 mL, for example, about 0.15 mL or about 0.2 mL. The culturing may be performed for about 10 hours or longer, about 20 hours or longer, about 30 hours or longer, about 40 hours or longer, about 50 hours or longer, about 60 hours or longer, about 70 hours or longer, about 80 hours or longer, or about 90 hours or longer.

The term "optical density" is synonymous with the term "absorbance" and refers to a proportion of light absorbed by a substance. The optical density A of the culture is measured at the first wavelength in the visible light range, and represents the sum of optical density of the microorganism and optical density of the cellulose. The optical density of the microorganism may be also called absorbance of the microorganism. The absorbance of the microorganism may represent a $\log(I_o/I_c)$ value of the microorganism present in the culture ($I_o$ is intensity of incident light and $I_c$ is intensity of transmitted light). The optical density of cellulose may be also called turbidity of cellulose. The turbidity of cellulose may represent a $\log(I_o/I_p)$ value of the cellulose present in the culture ($I_o$ is intensity of incident light and $I_p$ is intensity of transmitted light). The optical density B is measured at the second wavelength in the visible light range, and represents the optical density of the microorganism.

In the method, the optical density A and the optical density B of the culture may be measured simultaneously or sequentially. That is, measurement of the optical density B may be performed together with or after measurement of the optical density A. When the measurement of the optical density B is performed after the measurement of the optical density A, the measurement of the optical density B may be performed for all of the cultures of which the optical density A has been measured, or only the culture of which the optical density A is greater than that of the control group. The sequential measurement of the optical density may be measuring the optical density B with respect to only cultures, each of which has the optical density A being greater than that of a control group.

The method may further include dispersing cellulose in the culture, prior to measuring of the optical density. The dispersing may be achieved by applying vibration to the container containing the culture. The dispersing may be achieved by agitating or shaking the container containing the culture. The vibrating, or the agitating or shaking may be performed within about 10 seconds, about 8 seconds, about 6 seconds or about 5 seconds.

The measurement of the optical density may be performed for three times or more, four times or more, five times or more, or six times or more with respect to the same culture. The optical density may be a mean value of the remaining values excluding values showing a deviation of 5% or more, 7% or more, 10% or more, 12% or more, or 15% or more from values obtained by measuring optical density of the same culture three times or more, four times or more, five times or more, or six times or more. The optical density may be, for example, a mean value of the values showing a deviation of 10% or less, among values obtained by measuring optical density of the same culture three times or more.

The measurement of the optical density may be performed by a high throughput screening system. The measurement may be performed, together with the culturing, in a single high throughput screening system. The measurement of the optical density may be performed at any time after starting the culture. For example, the measurement of the optical density may be performed at about 10 hours, about 20 hours, about 30 hours, about 40 hours, about 50 hours, about 60 hours, about 70 hours, about 80 hours, or about 90 hours after start of the culturing. The measurement of the optical density may be performed during the culturing. The measurement of the optical density may be performed in real time during the culturing. From the result of the real-time measurement, initial cellulose production rates of various mutated strains may be compared.

In the measuring of the optical density, the first wavelength in the visible light range as used herein may be in the range of about 380 nm to about 420 nm, about 390 nm to about 410 nm, or about 395 nm to about 405 nm. The first wavelength may be, for example, about 400 nm. The second wavelength in the visible light range as used herein may be greater than the first wavelength, and may be in the range of about 750 nm to about 800 nm, about 760 nm to about 800 nm, about 770 nm to about 800 nm, about 780 nm to about 800 nm, or about 790 nm to about 800 nm. The second wavelength may be, for example, about 800 nm.

The method may further include culturing a microorganism having a ratio of optical density A/optical density B that is higher than that of the control group and obtaining a culture containing cellulose; and measuring a content of cellulose in the culture. The culturing may be a flask culturing.

In the culturing, a culture volume may be about 50 mL or more, about 40 mL to about 50 mL, about 30 mL to about 40 mL, about 20 mL to about 30 mL, or about 20 mL or less. The culturing may be performed in static culture or agitated culture. Appropriate culture conditions may be determined by those skilled in the art. A medium used in the culturing may be any general medium suitable for growth of the microorganism, such as a minimal or complex medium containing appropriate supplements. The suitable medium may be purchased from a commercially available source or prepared by a known preparation method. The medium may include ingredients selected from the group consisting of a carbon source, a nitrogen source, salts, trace elements, and combinations thereof. The carbon source may include monosaccharides, disaccharides and/or polysaccharides. The nitrogen source may be amino acids, amides, amines, nitrate, or ammonium salts. The medium may be an HS medium, a modified HS medium, an LB medium, modified LB medium, an YPD medium, a modified YPD medium, or a defined medium.

The culturing may be performed under aerobic conditions. The culturing temperature may be about 20 to about 40° C., about 22 to about 38° C., or about 25 to about 37° C. pH of the culture medium may be about 4.0 to about 7.5, about 4.0 to about 7.0, or about 4.5 to about 7.0. The culturing may be performed in a vented flask.

The measuring the content of cellulose may be performed after separating cellulose from the culture. The culture may be washed in order to separate cellulose. The content of cellulose means a dry weight of cellulose. By measuring the content of cellulose in the culture obtained from the flask culturing, it is further confirmed whether the microorganism having a high ratio of optical density A/optical density B compared to the control group actually has enhanced cellulose productivity, compared to the control group.

Another aspect provides a method of producing cellulose, the method including producing cellulose by culturing the microorganism having enhanced cellulose productivity, selected by the above defined screening method. Also, the produced cellulose may be recovered.

In the method of producing cellulose, the microorganism, optical density A, optical density B, culturing, and measuring are the same as described above with respect to the method of screening. The culturing may be a flask culturing. The flask culturing is the same as described above with respect to the method of screening.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects. As used herein, the term "and/or" includes any and all combinations of one or more of the associated listed items.

Hereinafter, one or more specific embodiments will be described in more detail with reference to Examples. However, these Examples are for illustrative purposes only, and the scope of the invention is not intended to be limited by these Examples.

Example 1: Measurement of Optical Density of Cellulose-Producing Strain

*Komagataeibacter xylinus* DSM 46604 strain was purchased from German Collection of Microorganisms and Cell Cultures GmbH (Deutsche Sammlung von Mikroorganismen and Zellkulturen GmbH (DSMZ)). HTS (Thermo Scientific/Liconic/Perkin Elmer) was used to culture the strain and to measure optical density. The optical density was measured at least three times to obtain mean values. From the obtained mean values, values showing a deviation of 10% or more were excluded, and the remaining values were used to obtain a mean value. Prior to each measurement, vibration was applied to the microplate for 5 seconds to mix cellulose well. In the following Examples, culturing of the strain and measurement of optical density will be performed in the same manner.

*Komagataeibacter xylinus* DSM 46604 strain was inoculated in a 96-well microplate containing 0.15 mL/well of Hestrin-Schramm (HS) medium containing 2 wt/vol % of glucose and 1 vol % of ethanol. Static culture was performed at 30° C. for 90 hours and optical density in a visible light range was measured every 8 hours.

FIG. 1 shows the result of measuring the optical density of the cellulose-producing strain in the visible light range. The optical density of the strain culture was measured according to a wavelength to obtain the solid line. This culture was immersed in 1N NaOH at 90° C. for 16 hours, and then completely washed with water to remove the strain and medium. The optical density of the culture free from the strain and medium was measured according to a wavelength to obtain a dotted line. The solid line represents the sum of the optical density of cellulose and the optical density of the strain, namely, turbidity of cellulose and absorbance of the strain. The dotted line represents only the turbidity of cellulose, and therefore, a difference between the solid line and the dotted line approximates the absorbance of the strain.

As shown in FIG. 1, the optical density of the strain has a higher value, whereas turbidity of cellulose has a lower value, at a longer wavelength, indicating that optical density measured at a long wavelength in the visible light range may be used to approximate density of the strain.

Example 2: Optical Density-Based Selection of Strain Having High Cellulose Productivity 2.1. Optical Density-Based Selection of Strain Having High Cellulose Productivity According to Example 1, a high optical density at a short wavelength (a first wavelength) in the visible light range indicates a high density of the strain or a high concentration of cellulose in the sample. Because the optical density at a long wavelength (a second wavelength) in the visible light range mainly represents absorbance of the strain, a relatively accurate density of the strain may be determined from the optical density measured at the long wavelength in the visible light range. On the basis of this, a method of selecting a strain having high cellulose productivity was developed as follows:

(1) (a) measuring an optical density A of a culture of a strain at a first wavelength in a visible light range, or (b) measuring an optical density A of a culture of a strain at a first wavelength in a visible light range and also measuring an optical density B of the strain at a second wavelength in the visible light range.

(2) in the case of (a) measuring an optical density B of the strain at a second wavelength in the visible light range and calculating a ratio of (optical density A)/(optical density B), or in the case of (b) calculating a ratio of (optical density A)/(optical density B).

(3) Selecting a strain with a ratio of (optical density A)/(optical density B) greater than that of a control group.

2.2. Preparation of Mutant Strain and Measurement of Optical Density

Mutant strains of *Komagataeibacter xylinus* DSM 46604 were prepared by random mutagenesis using N-methyl-N'-nitro-N-nitrosoguanidine (NTG). NTG was completely dissolved in acetone at a concentration of 10.0% (w/v) and distilled water was added to prepare a NTG solution at a final concentration of 1.0% (w/v). A parent strain *Komagataeibacter xylinus* DSM 46604 was cultured for 24 hours in a 50 mL-tube containing 10 mL of HS medium containing 2 wt/vol % of glucose and 1 vol % of ethanol. NTG solution was added thereto at a final concentration of 30 μg/mL and cultured for 50 minutes at 34° C. and 250 rpm. Then, centrifugation was performed at 4,000 rpm for 7 minutes to remove a supernatant, and a cell pellet was washed with HS medium (20 ml) twice to remove NTG. 10 ml of HS medium was added to the NTG-removed tube, and the cells were incubated at 30° C. and 250 rpm for 24 hours, and then spread on an HS solid agar medium. The solid medium was incubated at 30° C. for 72 hours to obtain colonies of mutant strains.

The parent strain and mutant strains were inoculated in a 96-well microplate containing 0.15 mL/well of HS medium, and static culture was performed at 30° C. for 72 hours. Then, optical density A at 400 nm and optical density B at 800 nm were measured. Measurement of optical density was repeated at least three times to obtain mean values. From the obtained mean values, values showing a deviation of 10% or more were excluded, and the remaining values were used to obtain a mean value. Prior to each measurement, vibration was applied to the microplate for 5 seconds to mix cellulose.

2.3. Reliability Test

To test the reliability of the optical density-based method, the mutant strains obtained in Example 2.2 were cultured in flasks under the same conditions and their cellulose productivity was measured.

The parent strain and mutant strains were cultured in 250 mL-flasks containing 50 mL of HS medium containing 2 wt/vol % of glucose and 1 vol % of ethanol 72 hours at 34° C. and 250 rpm. After culturing, produced cellulose was immersed in 200 mL of 1N NaOH at 90° C. for 16 hours, and then completely washed with water to remove the strain and medium. The washed cellulose was freeze-dried to measure the weight. A value predicted by the optical density-based method and an actual production amount of cellulose were compared by the following equation.

Correlation (% ratio)=(amount of cellulose$_{mutant\ strain}$−amount of cellulose$_{parent\ strain}$) %÷(ratio of optical density$_{mutant\ strain}$−ratio of optical density$_{parent\ strain}$) %

Herein, (amount of cellulose$_{mutant\ strain}$−amount of cellulose$_{parent\ strain}$)% is (amount (mg) of cellulose actually produced by the mutant strain in flask−amount (mg) of cellulose actually produced by the parent strain in flask)÷amount (mg) of cellulose actually produced by the parent strain in flask×100. (ratio of optical density$_{mutant\ strain}$−ratio of optical density$_{parent\ strain}$) % is (ratio (A/B$_{mutant\ strain}$) of optical density of mutant strain measured in microplate−ratio (A/B$_{parent\ strain}$) of optical density of parent strain measured in microplate)÷ratio (A/B$_{mutant\ strain}$) of optical density of mutant strain measured in microplate×100.

Figure 2:
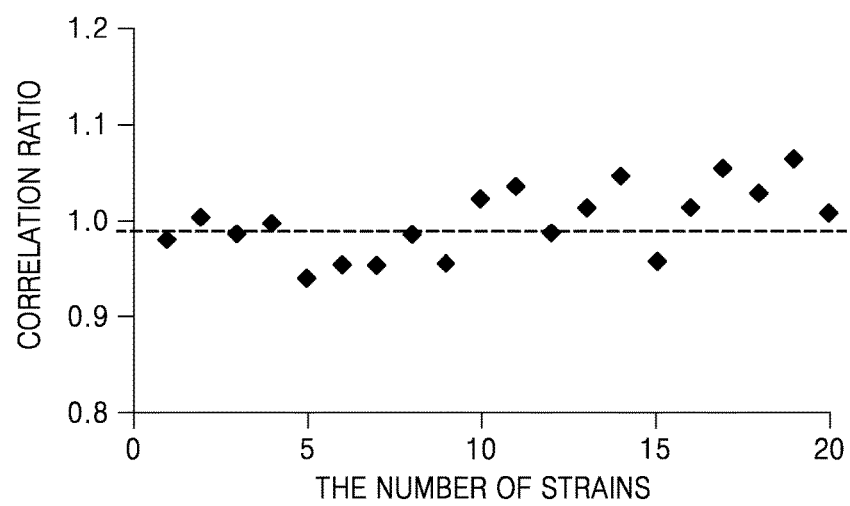
FIG. 2 is a graph showing a correlation between a value predicted by an optical density-based method and actual cellulose productivity.

FIG. 2 is a graph showing a correlation between the value predicted by the optical density-based method and actual cellulose productivity. As shown in FIG. 2, a correlation between the value predicted by the optical density-based method and actual cellulose productivity was about 95.4%. The result of FIG. 2 suggests that the optical density-based method may be effectively used to select strains having increased cellulose productivity.

Example 3: Optical Density-Based Selection of Strain Having High Cellulose Productivity Mutant strains of *Komagataeibacter xylinus* DSM 46604 were prepared in the same manner as in Example 2.2. Colonies of 1,800 types of mutant strains were inoculated in a 96-well microplate containing 0.15 mL/well of HS medium, and static culture was performed at 30° C. for 90 hours. Then, optical density at 400 nm was measured. Measurement of optical density was repeated at least three times to obtain mean values. From the obtained mean values, values showing a deviation of 10% or more were excluded, and the remaining values were used to obtain a mean value. Prior to each measurement, vibration was applied to the microplate for 5 seconds to mix cellulose.

5 types of strains having greater optical density at 400 nm than that of the parent strain were selected. To exclude the high optical density attributed to high density of the strain, optical density at 800 nm was measured with respect to the selected 5 types of the strains to calculate a ratio of (optical density at 400 nm)/(optical density at 800 nm).

Figure 3A:
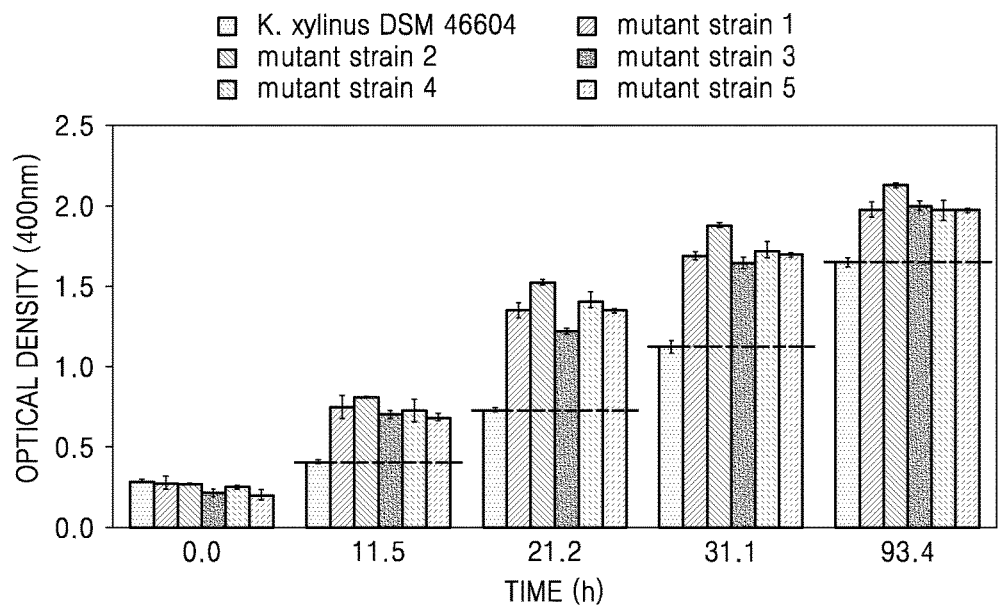
FIG. 3A shows an optical density at 400 nm of a parent strain and 5 types of mutant strains.
Figure 3B:
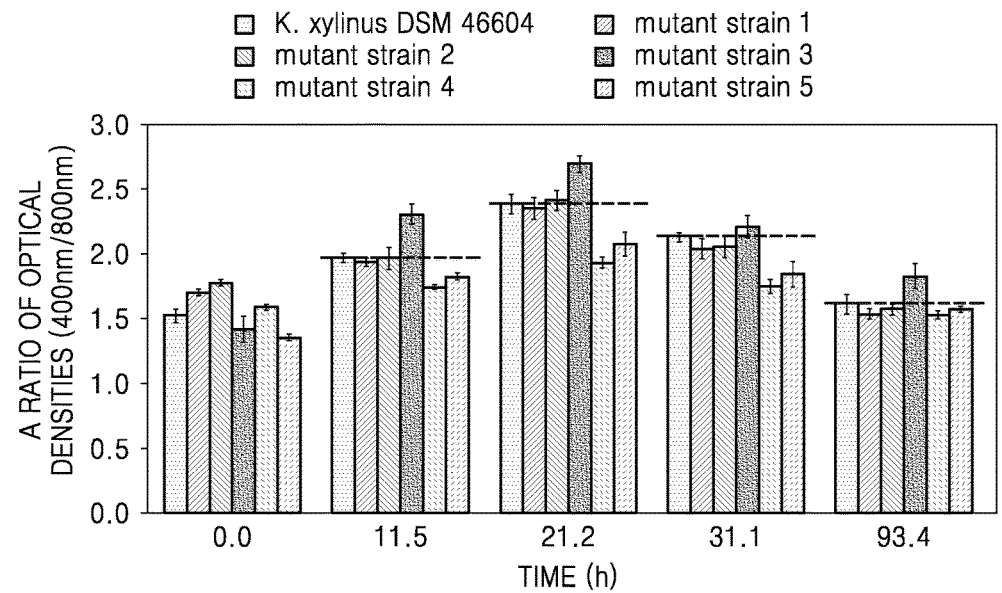
FIG. 3B shows a ratio of (optical density at 400 nm)/(optical density at 800 nm) of the strains of FIG. 3A.

FIG. 3A shows an optical density at 400 nm of the parent strain and 5 types of mutant strains. FIG. 3B shows a ratio of (optical density at 400 nm)/(optical density at 800 nm) of the strains of FIG. 3A. As shown in FIG. 3B, a type of mutant strain was found to have a higher ratio of (optical density at 400 nm)/(optical density at 800 nm) than that of the parent strain. Therefore, this mutant strain was selected as a strain having enhanced cellulose productivity, compared to the parent strain.

The amount of cellulose actually produced by the selected mutant strain was measured, and as a result, the strain shows about 10% increase in the production amount, compared to the parent strain, indicating that a strain having excellent cellulose productivity may be selected by the optical density-based method.

It should be understood that the exemplary embodiments described herein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A method of screening for a microorganism having enhanced cellulose productivity, the method comprising:
   culturing mutated or recombinant cellulose-producing microorganisms to obtain a plurality of cultures containing the respective microorganisms and produced cellulose;
   culturing one or more non-genetically modified and non-mutated cellulose-producing microorganisms to provide at least one respective control group;
   measuring an optical density A of each respective control group and each culture of the one or more mutated or recombinant cellulose producing microorganisms, wherein the optical density A is an optical density at a first wavelength in a visible light range of about 380 nm to about 420 nm;
   measuring an optical density B of each respective control group and at least one mutated or recombinant cellulose producing microorganism, wherein the optical density B is an optical density at a second wavelength in the visible light range of about 750 nm to about 800 nm;
   obtaining a ratio of optical density A/optical density B with respect to cultures that have an optical density A being greater than that of said respective control group; and
   selecting a mutated or recombinant microorganism that has a ratio of optical density A/optical density B greater than that of said respective control group as a microorganism having enhanced cellulose productivity.

2. The method of claim 1, wherein the cellulose-producing microorganisms comprise a microorganism belonging to *Gluconacetobacter* sp.

3. The method of claim 1, wherein the mutated microorganism is produced by random mutagenesis.

4. The method of claim 1, wherein the microorganisms are cultured in the wells of a microplate.

5. The method of claim 1, wherein the optical density B is measured only with respect to cultures in which the optical density A is greater than that of the respective control group.

6. The method of claim 1, further comprising dispersing the produced cellulose in the culture prior to measuring the optical density A or the optical density B.

7. The method of claim 1, wherein each of the optical density A and the optical density B is a mean value of three or more measurements with a deviation of 10% or less.

8. The method of claim 1, wherein the optical density A and the optical density B are measured by a high throughput screening system.

9. The method of claim 1, wherein the optical density A and the optical density B are measured during culturing.

10. The method of claim 1, further comprising:

culturing the selected mutated or recombinant microorganism having a ratio of optical density A/optical density B higher than that of the control group to obtain a culture containing cellulose; and measuring a content of the cellulose in the culture.

11. A method of producing cellulose, the method comprising:

selecting a mutated or recombinant microorganism according to the method of claim 1;

culturing the mutated or recombinant microorganism to produce cellulose; and recovering the cellulose from the culture.

12. The method of claim 11, wherein the culturing is performed in flasks.

* * * * *